United States Patent
Sun et al.

(10) Patent No.: US 6,668,188 B2
(45) Date of Patent: Dec. 23, 2003

(54) DETERMINATION OF LONG-TERM CONDITION OF CARDIAC PATIENTS

(75) Inventors: Weimin Sun, Plymouth, MN (US); Bruce KenKnight, Maple Grove, MN (US); Jeffrey A. Hall, Birmingham, AL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 238 days.

(21) Appl. No.: 09/843,303

(22) Filed: Apr. 25, 2001

(65) Prior Publication Data

US 2002/0161412 A1 Oct. 31, 2002

(51) Int. Cl.[7] ............................................. A61B 5/0402
(52) U.S. Cl. ........................... 600/513; 607/19; 600/523
(58) Field of Search ....................... 607/17–25; 600/510, 600/513–518, 523

(56) References Cited

U.S. PATENT DOCUMENTS

4,374,382 A  2/1983  Markowitz
4,825,869 A  5/1989  Sasmor et al.
5,081,987 A  1/1992  Nigam
6,058,329 A  5/2000  Salo et al.

*Primary Examiner*—Jeffrey R. Jastrazab
(74) *Attorney, Agent, or Firm*—Nikolai & Mersereau, P.A.; C. G. Mersereau (57) ABSTRACT

A method of presenting information for evaluating the condition of chronically impaired cardiac patients based on long-term assessment of activity trends, using a memoried implanted cardiac rhythm management device having a plurality of programmable parameters and one or more sensors for sensing one or more parameters related to an activity level of the patient. The method includes acquiring sensor signal data indicative of the activity level of the patient, accumulating sensor signal data in memory and using the accumulated sensor signal data to determine the activity level of the patient during a predetermined period of time, recording the activity level during a plurality of sequential time periods, adding contemporary annotation information to the activity data and producing a data record of the activity level with the annotation information during sequential time periods sufficient to indicate trends in a patient's activity level.

20 Claims, 6 Drawing Sheets

DETERMINATION OF LONG-TERM CONDITION OF CARDIAC PATIENTS

BACKGROUND OF THE INVENTION

I. Field of the Invention

The present invention relates to a concept for long-term assessment of the condition of chronically impaired cardiac patients, generally, and particularly pacemaker patients. The concept is based on the integrated presentation of information related to activity level over an extended time period sensed by an implanted cardiac rhythm management system such as a pacemaker device, together with information collected by one or more related sensors presented with annotations of related events as a composite representation.

II. Related Art

Early cardiac pacemakers were used primarily to pace the heart when the normal conduction path from the sinoatrial (SA) node of the heart to the atrial ventricular (AV) node or from the AV node to the ventricles was interrupted. In accordance with these events, the pacemaker was called upon to deliver ventricular stimulating pulses to maintain a predetermined heart rate. More recently, pacemaker technology has become greatly advanced and much more sophisticated. For example, rate adaptive pacing has been used to vary the predetermined rate in accordance with parameters indicative of patient activity level. Pacing has also been used to optimize hemodynamic performance in patients suffering from congestive heart failure (CHF) or other left ventricle dysfunction.

It has also become of interest to monitor the level of activity of a patient over prolonged periods of time as it has become well recognized that the general level of activity and the activity profile are indicative of the well-being and prognosis of the patient. In the case of a CHF patient, for example, a direct correlation has been shown between the level of activity and condition. Historically, such activity has been evaluated using quality of life questionnaires and various exercise tests such as the "Six-Minute Walk Test" in which the distance traversed by a patient walking a level path for six minutes is measured. While this and other stress-type tests have provided valuable information, they must be administered by physicians and so require frequent trips to the physicians' office and they do not provide any on-going monitoring function.

Activity levels can, for example, be measured by means of an accelerometer affixed to the patient which provides data that can be used in assessing the patient's wellbeing. Such a system is shown in co-pending application Ser. No. 09/076,025, filed May 11, 1998, entitled "METHOD AND APPARATUS FOR ASSESSING PATIENT WELL-BEING", assigned to the same assignee as the present application and incorporated herein by reference for any purpose.

That disclosure shows that an accelerometer can be used to determine whether a change in the mode of pacing a CHF patient is beneficial to the overall well-being of the patient. The assessment can be based on intermittent short-term monitoring using an accelerometer sensor and relating it to the level of activity of the patient at that moment.

Pacing devices have also been provided with a memory function to receive and store sensed data relative to cardiac activity which can later be recalled and utilized. Examples of this can be found, for example, in U.S. Pat. No. 5,081,987 to Nigam which uses telemetric transmission of such data for use in a separate external data processor.

While limited practical use has been made of techniques for assessing the well-being of cardiac patients wearing pacing devices, there remains a definite need to monitor patient activity over substantial periods of time to determine longer term trends. In this manner, changes in lifestyles can be seen and overall wellness can be monitored. Trends in patient activity levels indicative of these factors could be presented. It would also be beneficial if additional data regarding events which might affect an evaluation be simultaneously presented and the combination utilized to assess the general condition of the patient and to evaluate outcomes of adjustments in therapy related to the management of the disease.

SUMMARY OF THE INVENTION

The present invention involves gathering information and integrating the information to generate an annotated activity chart that enables a physician to track and interpret a CHF patient's relative wellness. The integrated data of the chart provides information that allows an assessment of outcomes of therapy and changes or adjustments in therapy over time to thereby provide a tool to enable better overall disease management. The invention involves a method of monitoring the activity of a paced patient over an extended period of time thereby noting general changes in lifestyle and relative wellness and displaying data accumulated in that manner, together with annotations indicative of events of interest during the monitored period. A plurality of individual monitoring periods are averaged and recorded and a plurality of successive periods is used to generate an activity chart to show a patient's overall activity within a longer duration.

The detailed example makes use of the method as applied to a pacing device provided with a plurality of programmable parameters in conjunction with one or more sensors for sensing one or more parameters indicative of the activity level and cardiac function of the patient. Sensor signal data is accumulated and stored in memory over each selected interval or period of interest and a function of that accumulated data is used to represent activity of the patient during that period of interest. Such data records are produced for a sequence of such time periods accumulating sufficient successive relative activity values to produce a data record or chart indicative of trends in the activity level of the patient over a longer duration.

Additional data in the form of annotations recording contemporaneous events which occur during the course of an interval or period of interest are included to provide a more comprehensive representation of wellness data over the longer duration presented in a combined comprehensive representation. The present invention enables evaluation from a single presentation of combined data which may be a histographic representation.

ADVANTAGES OF THE INVENTION

Accordingly, the present invention advantageously provides a method of assessing or evaluating trends in the relative condition or wellness of a chronotropically incompetent patient by observing trends in the activity of the patient over an extended period of time using a single representation of several kinds of data.

The invention also portrays long-term trends in the activity of a patient by charting successive periodic peak or periodically averaged values of activity levels based on shorter durations.

The present invention includes the advantage of including annotated activity chart data to combine a chronology of events of interest with the charted values of activity levels to provide a composite marker channel to aid the physician in interpreting the condition of a patient and assessing therapy outcomes.

DETAILED DESCRIPTION

As an overview, the present invention provides important long-term insight useful in tracking and interpreting the wellness of a patient having an implanted rate-adaptive pacing device in a convenient form. This is accomplished by providing comprehensive data which over an extended time period includes information that indicates trends in the average activity level of the patient. The trends may be indicated by histographic charts recording successive periodic peak or periodically averaged values of activity levels which are derived by monitoring one or more activity level related parameters. The charted values are also preferably provided with annotations related to significant contemporary events which might influence evaluation of collected data. Such may include, for example, the starting and ending of the administration of a therapeutic drug (ACE, hypertension drug, anti-arrhythmia drug, etc.); atrial tachycardia response and atrial tachycardia incidence counts; atrial fibrillation counts; incidences of angina, dispenia, palpitation or other discomforts; special device therapy such as anti-tachy pacing, cardioversion or shock; counts of device telemetry connections; and time of device implants, follow-up or additional clinic visits, or the like.

With relation to drug use, a notation of drug prescription inception may be entered into the electronic data stream at the proper time and a notation of discontinuance may be appropriately entered at that time as well. The atrial tachycardia response and tachycardia incidence counts may be linked to a stored electrogram (EGM) which can be recalled if details are desired. Atrial fibrillation counts can be linked to a data-entry showing time and duration of the atrial fibrillation incident. The counts of device telemetry connections can be stored in a telemetry log which can later be recalled as desired.

The long-term averaged activity signal-related parameter is indicative of activity levels are preferably presented as a histogram or bar chart or as plotted bar chart data so that any long-term trends are easily detected. However, any of several activity presentation formats that provide intuitive and systematic information on the patient's condition and activity patterns may be used. For example, on a histogram chart, one or more of the following data can be grouped together:

(a) weekly activity histogram of the patient;
(b) monthly activity histogram of the patient;
(c) weekly or monthly activity histogram of normal population; and
(d) device rate adaptive therapy parameters.

The sensed activity levels can be based on signal amplitudes, blended sensor amplitudes, spectrum components or blended spectrum components of one or more sensors per an accelerometer, minute-ventilation, etc. The activity levels may be peak levels reached during an interval or averaged levels which are averaged daily, weekly monthly or for any desired interval and each averaged activity level bar can be annotated with a brief abbreviated message which is hyper-linked to a stored electrogram, a physician's note or other device-generated data assembly.

The invention can be implemented using any rate-adaptive, microprocessor-controlled programmable pacing system and sensor combination capable of acquiring and storing the requisite data and communicating through an input/output (IO) interface with an external monitor/output device and programming system. The acquired, stored data can be presented in any manner that will facilitate desired evaluation. The implementation further described next is offered as being exemplary of, but with no intent to limit the inventive concept.

Figure 1:
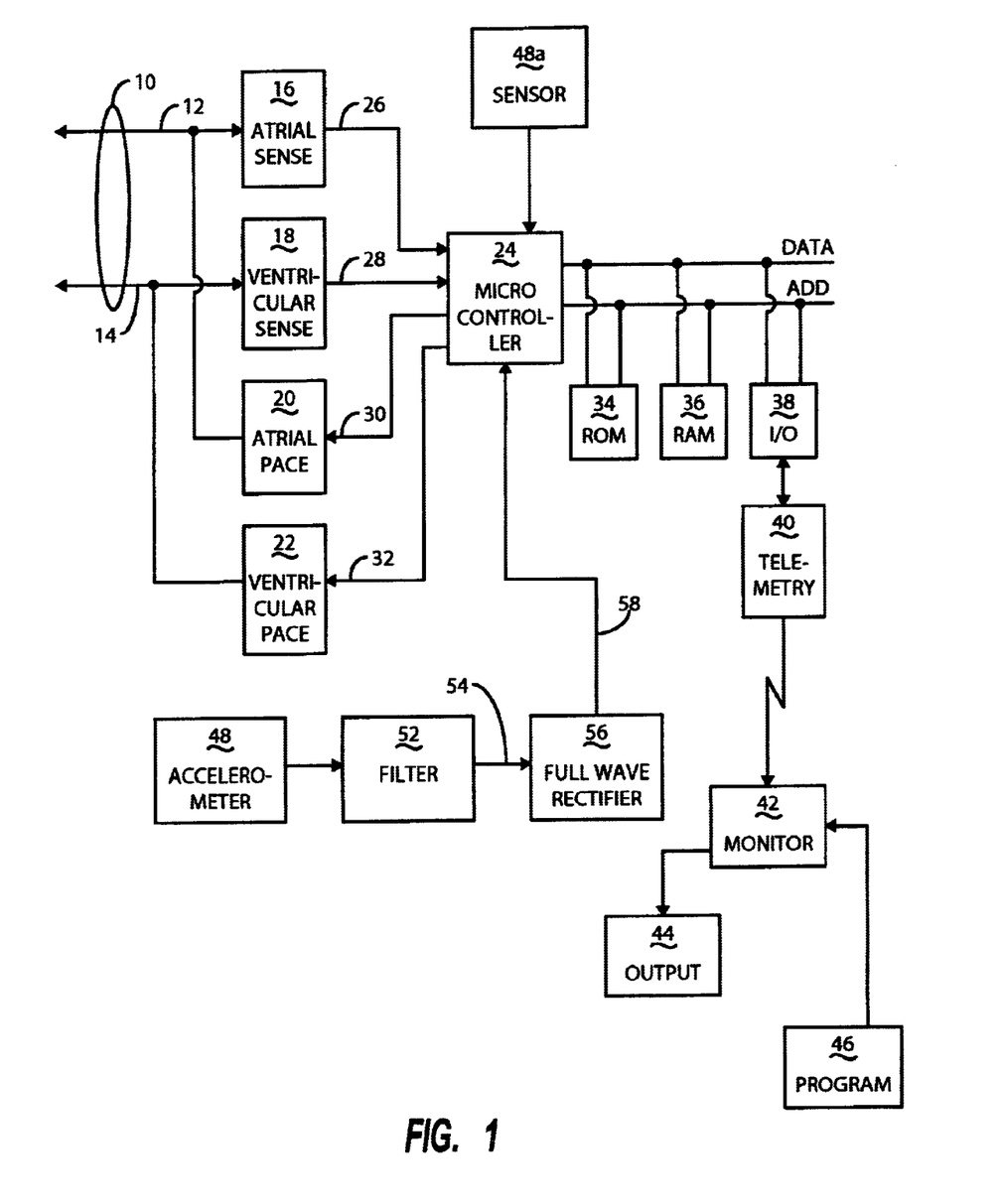
FIG. 1 is a schematic diagram showing one example of a pacing system which may be used to practice the invention.
Figure 2:
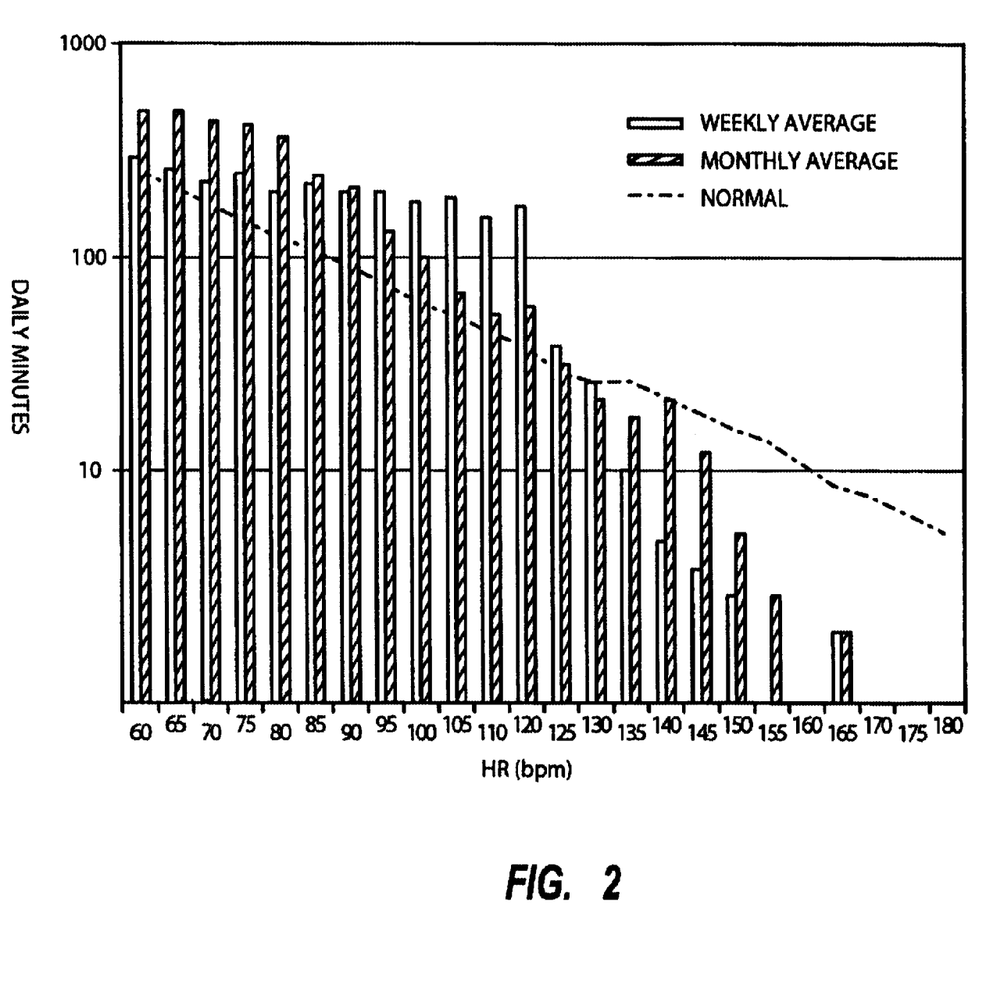
FIG. 2 is a composite bar chart depicting daily minutes at various heart rates in beats per minute (bpm) averaged over weekly and monthly periods for a patient, including a comparison with a hypothetical indicated population norm.
Figure 3:
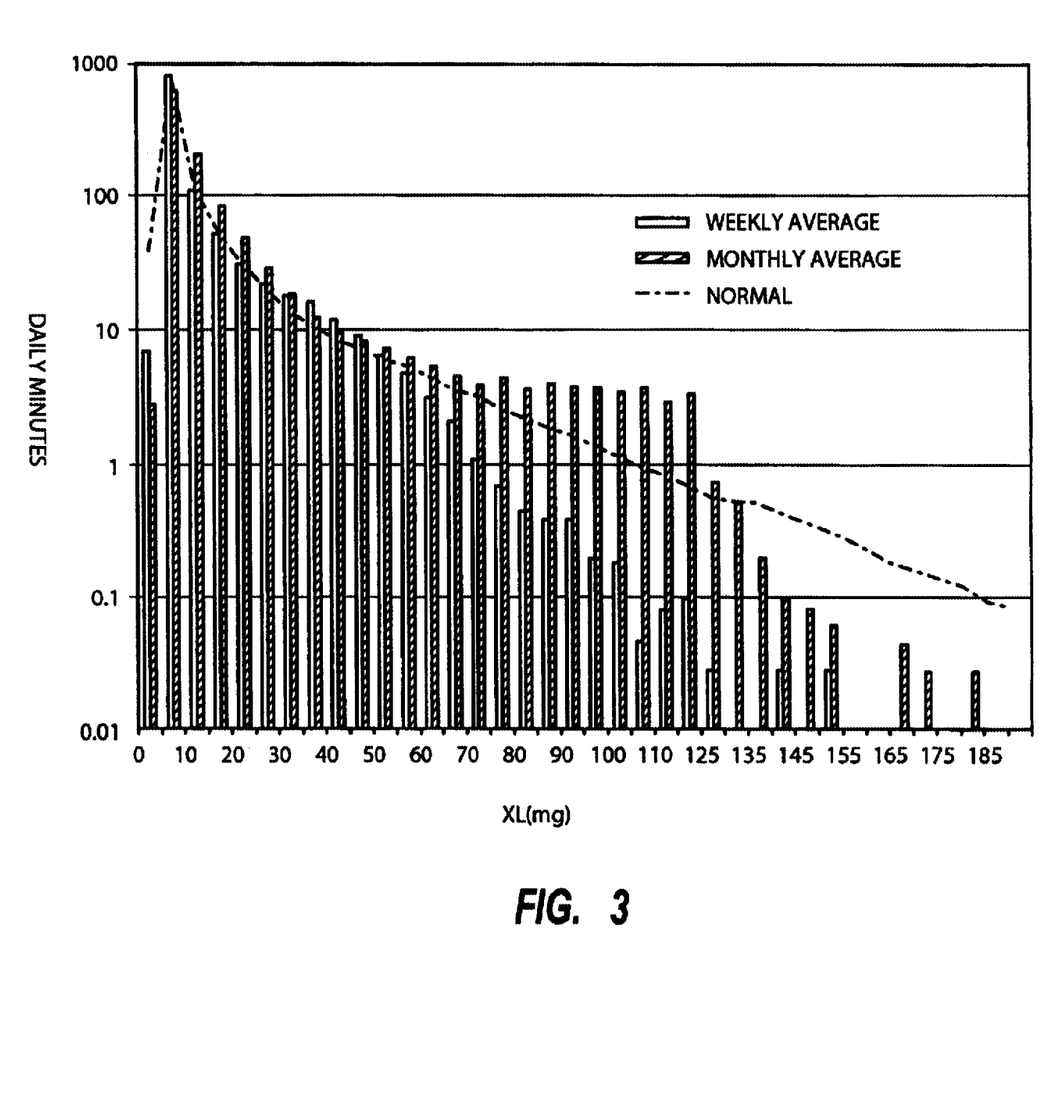
FIG. 3 is a composite bar chart similar to that of FIG. 2 using accelerometer readings in mini-gravity (mg) units instead of heart rate.
Figure 4:
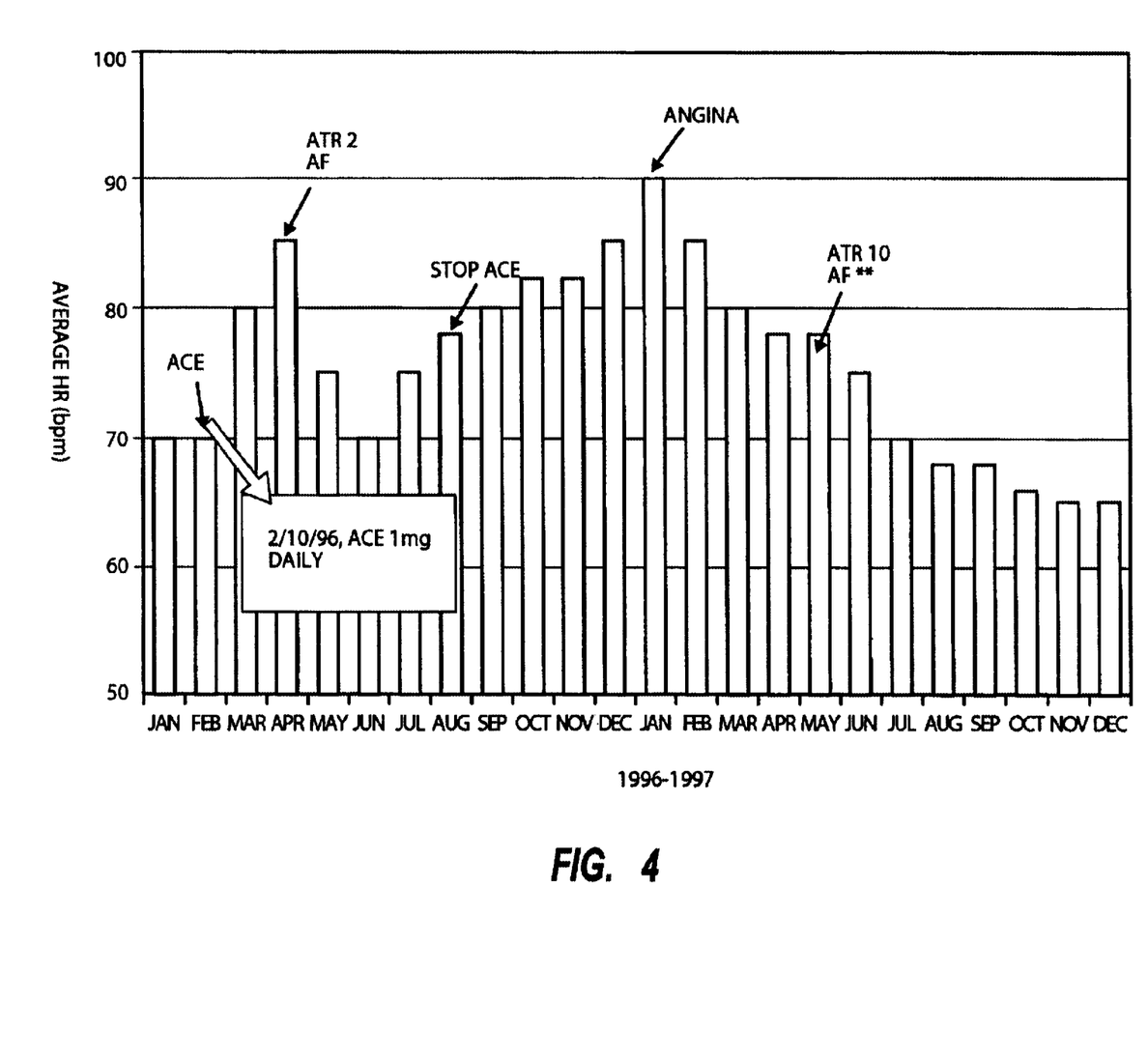
FIG. 4 is a bar chart of monthly average heart rate (bpm) over a two-year span with annotations indicated as to events of interest.
Figure 5:
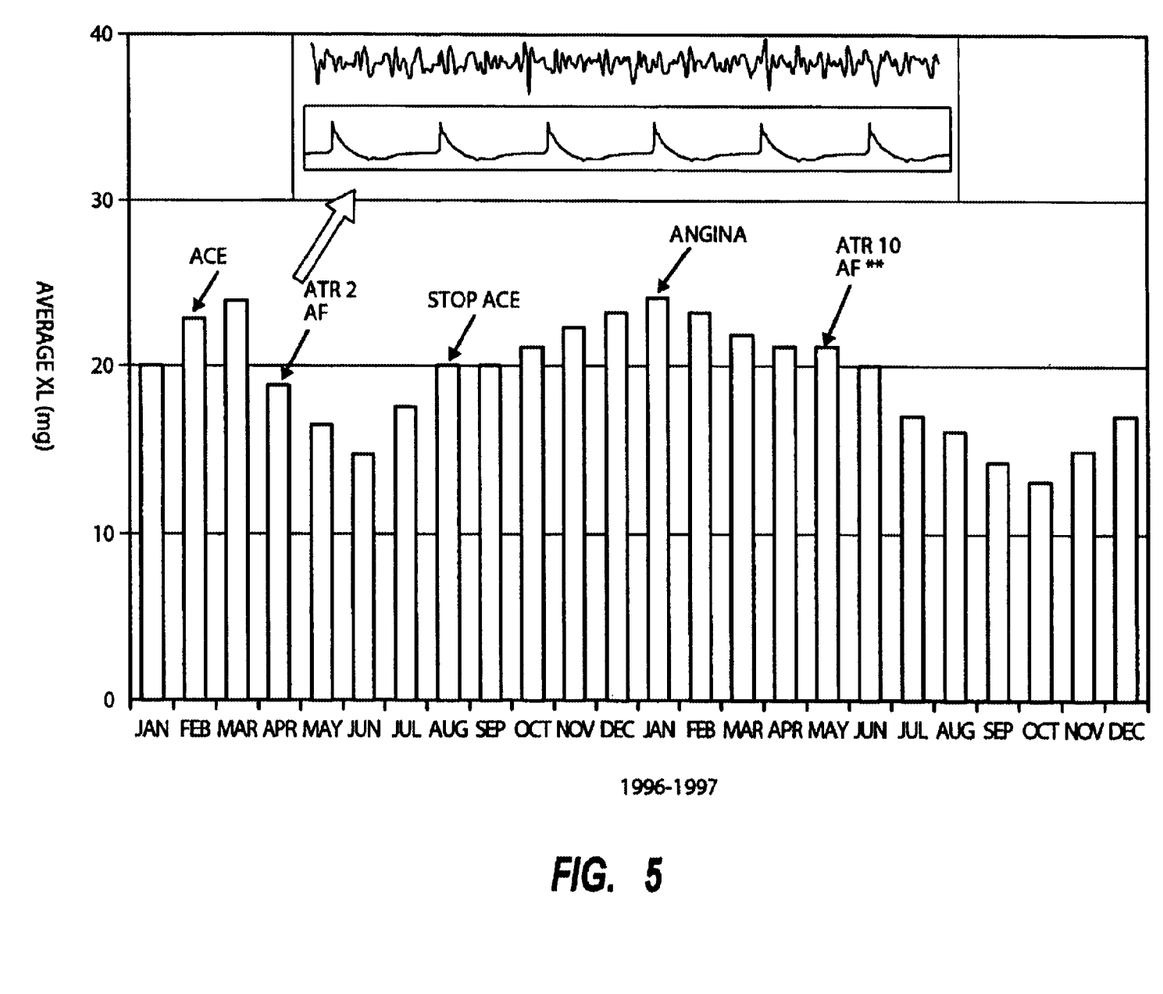
FIG. 5 is a bar chart similar to that of FIG. 4 using average accelerometer readings (mg) instead of heart rate and further depicting electrogram (EGM) related to one annotated incident.
Figure 6:
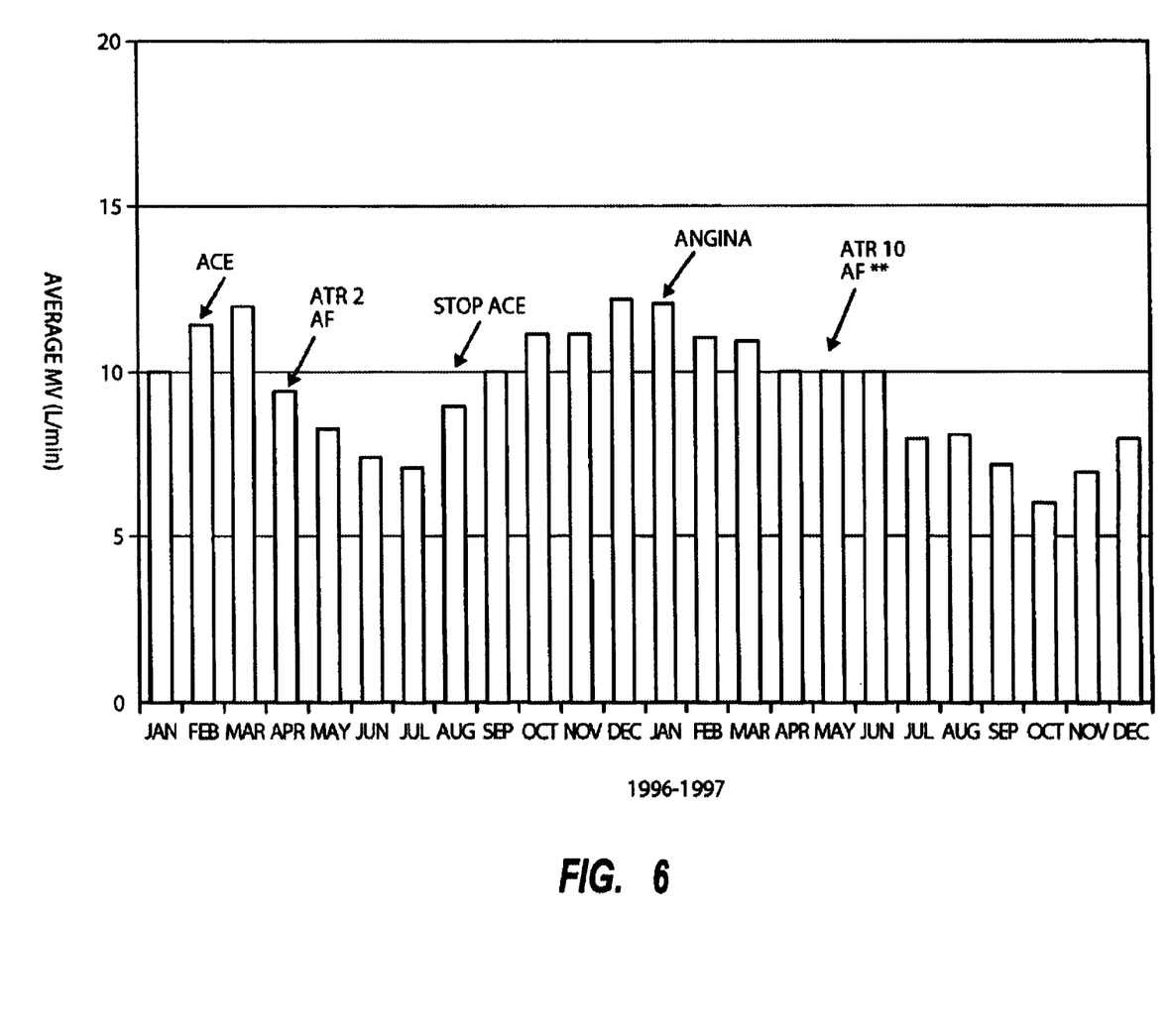
FIG. 6 is an annotated bar chart similar to that of FIG. 4 and depicting average minute ventilation (mv) in liters/minutes (L/Min).

FIG. 1 illustrates a representative apparatus that may be utilized to practice the present invention in block diagram form. The system includes a dual chamber pacemaker with pacing leads 10 having electrodes (not shown) for placement in endocardial or myocardial tissue and insulated conductors 12 and 14 used to carry electrical signals to and from the electrodes. Leads such as conductor 12 typically connect to an electrode positioned to sense and stimulate the atrial chamber and conductor 14 carry electrical signals to and from one or more electrodes position to stimulate the right ventricle or the left ventricle or both the right and the left ventricles in case of bi-ventricular pacing.

The system further includes an atrial sense amplifier 16, a ventricular sense amplifier 18, an atrial stimulating pulse generator 20 and a ventricular pacing pulse generator 22. As is well known to those skilled in the art, the atrial sense amplifier circuitry 16 detects atrial depolarization events (P-waves) while the ventricular sense circuit 18 detects ventricular depolarization events (R-waves). The outputs from the atrial and ventricular sense amplifiers are carried to a microprocessor-based controller or micro-controller 24 using conductors 26 and 28, respectively.

During operation of the system, the micro-controller 24 responds to the inputs and dispatches appropriate control signals over lines 30 and 32 to cause the atrial pulse generator 20 and the ventricular pulse generator 22 to, in turn, produce cardiac stimulating pulses at times determined by software programmed into the microcontroller's ROM memory 34. Other data, including a variety of sensed data and the like, are typically stored in a RAM memory 36. This may also include alterable operating parameters for the pacemaker. The micro-controller 24 and memories 34 and 36 further connected with an input/output device 38 which uses a telemetry link to connect the system to an external monitor 42 or output device 44 and an instructing or programming device 46. The output device 44 may be a printer, for example, which prints an integrated histogram of patient data, as shown in any of FIGS. 2–6.

The system is further provided with one or more additional sensing devices depicted here as an accelerometer at 48 and another sensor 48a. The accelerometer is located within the moisture impervious hermetically sealed housing or can of the pacemaker which itself is implanted so as to accentuate the vibratory force components desired to be sensed by the accelerometer 48. The output of the accelerometer 48 is typically a raw accelerometer signal which appears on line 50 that may include heart sounds, components due to chest wall movement due to respiratory activity and components due to other internal and external sources of acoustic energy. This raw signal is subjected to a filter 52 which filters out unwanted components of the signal and applies the filtered signal on line 54 to a rectifier at 56 which, in turn, reduces the bi-polar signal to a mono-polar output signal on line 58 and applies it as an input to the micro-controller 24 where it is digitized and coordinated in time with a desired sensing signal from line 26 or 28. The filter 52 may be one designed to pass or block any band so that the desired detected signals are retained and unwanted components blocked. As shown in 48a, the sensor of interest may connect directly with the micro-controller and have A/D and other signal processing be carried out in the micro-controller.

This data may be accumulated over time and a peak value selected or the data may be averaged as desired to produce the processed data necessary to the later production of the bar charts in accordance with FIGS. 2–6. Annotations generally may be entered utilizing the programming device 46 contemporaneously with the occurrence of events to be noted. Other events may be intrinsically sensed by the system sensors. It will be appreciated that the annotated charts can depict in a single presentation an integrated presentation of drug use and dose, arrhythmic episodes and real time EGM, discomfort complaints (angina, syncope, etc.), therapy history (ATR, ATP, CV, shock, etc in addition to activity level and fitness.

The desired stored data may be made available through the telemetry and monitoring system to an output device where it can be presented graphically or otherwise as desired and made available to produce the bar charts and histograms illustrated in FIGS. 2–6 in accordance with the invention. The combined presentation gives the physician a powerful tool to assess the patient's progress and the relative success of therapy strategies.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, for example, data may be gathered by an implanted defibrillator and that various modifications, both as to the equipment details and operating procedures, can be accomplished without departing from the scope of the invention itself.

What is claimed is:

1. A method of presenting information for evaluating the condition of chronically impaired cardiac patients based on long-term assessment of activity trends, using a memoried implanted cardiac rhythm management device providing one or more sensors for sensing one or more parameters related to an activity level of the patient comprising the steps of:
    (a) acquiring sensor signal data indicative of the activity level of the patient;
    (b) accumulating sensor signal data in memory and using the accumulated sensor signal data to determine the activity level of the patient during a predetermined period of time;
    (c) recording the activity level based on data selected from the group consisting of heart rate and accelerometer readings during a plurality of sequential time periods;
    (d) adding contemporary annotation information to the activity data;
    (e) producing a histogram chart of the activity level using data selected from the group consisting of heart rate and accelerometer readings with said annotation information during sequential time periods sufficient to indicate trends in a patient's activity level; and
    (f) wherein the data displayed further includes a representation of normal population average value.

2. A method as in claim 1 wherein the activity level selected is from the group consisting of peak activity level and average activity level during a predetermined period of time.

3. A method as in claim 2 wherein the activity level selected is the average activity level.

4. A method as in claim 2 further including the use of an accelerometer as a sensor in acquiring sensor signals.

5. A method as in claim 2 wherein the sequential time periods are selected from days, weeks and months.

6. The method as in claim 1 wherein the annotation information is selected from the group consisting of drug use and dosage, arrhythmia episode and related real-time EGM, activity level and fitness, discomfort complaints, therapy history and combinations thereof.

7. A method as in claim 6 wherein the selected activity level is the average activity level.

8. A method as in claim 1 wherein the chart represents cumulative daily minutes for each of a plurality of heart rates averaged on a basis selected from the group consisting weekly and monthly averages and wherein the chart includes a representation of a normal population average value.

9. A method as in claim 1 further including the use of an accelerometer as a sensor and wherein the chart represents cumulative daily minutes for each of a plurality of accelerometer readings averaged on a basis selected from the group consisting weekly and monthly averages and wherein the chart includes a representation of a normal population average value.

10. A patient histogram record developed using the method of claim 1.

11. The patient histogram record as in claim 10 wherein the selected activity level is from the group consisting of peak and average activity level during a predetermined period of time.

12. The patient histogram record as in claim 11 wherein the annotation information selected from the group consisting of drug use and dosage, arrhythmia episode and related real-time EGM, activity level and fitness, discomfort complaints, therapy history and combinations thereof.

13. The patient histogram record as in claim 12 further comprising an indicator of a representative normal population value.

14. The patient histogram record as in claim 11 further comprising an indicator of a representative normal population value.

15. A method of evaluating the condition of chronically impaired cardiac patients based on long-term assessment of activity trends using a memoried implanted cardiac rhythm management device having a plurality of programmable parameters to a patient and providing one or more sensors for sensing one or more parameters related to the activity level of the patient, the method comprising the steps of:

(a) acquiring sensor signal data indicative of the activity level of the patient;

(b) accumulating sensor signal data in memory and using accumulated sensor signal data selected from the group consisting of heart rate and accelerometer readings to determine the average activity level of the patient during a predetermined period of time;

(c) recording the average activity level during a plurality of sequential time periods;

(d) producing a chart of the average activity level using data selected from the group consisting of heart rate and accelerometer readings during sequential time periods sufficient to indicate trends in a patient's average activity level;

(e) presenting the data record as a histogram chart;

(f) adding contemporary annotation information to the average activity histogram chart and (g) adding an indicator of a normal population average value.

16. A method as in claim 15 wherein the annotation information is selected from the group consisting of drug use and dosage, arrhythmia episode and related real-time EGM, activity level and fitness, discomfort complaints, therapy history and combinations thereof.

17. A method as in claim 16 further including the use of an accelerometer as a sensor and wherein the chart represents cumulative daily minutes for each of a plurality of accelerometer readings averaged on a basis selected from the group consisting weekly and monthly averages.

18. A method as in claim 17 wherein said implanted cardiac rhythm management device is a rate-adaptive cardiac pacing device, said method further comprising the step of adjusting operating parameters in said rate-adaptive cardiac pacemaker as indicated by changes in activity trends.

19. A method as in claim 15 wherein the chart represents cumulative daily minutes for each of a plurality of heart rates averaged on a basis selected from the group consisting weekly and monthly averages and wherein the chart includes a representation of a normal population average value.

20. A method as in claim 19 wherein said implanted cardiac rhythm management device is a rate-adaptive cardiac pacing device, said method further comprising the step of adjusting operating parameters in said rate-adaptive cardiac pacemaker as indicated by changes in activity trends.

* * * * *